United States Patent
Rothenberg et al.

(10) Patent No.: US 10,982,980 B2
(45) Date of Patent: Apr. 20, 2021

(54) METHOD AND DEVICES FOR SIGNIFYING SCRUBBING ACTION

(71) Applicant: CAREFUSION 2200, INC., San Diego, CA (US)

(72) Inventors: Ashley Rothenberg, Morris Plains, NJ (US); Nathan Sieracki, Deerfield, IL (US)

(73) Assignee: CAREFUSION 2200, INC., San Diego, CA (US)

(*) Notice: Subject to any disclaimer, the term of this patent is extended or adjusted under 35 U.S.C. 154(b) by 644 days.

(21) Appl. No.: 15/829,587

(22) Filed: Dec. 1, 2017

(65) Prior Publication Data

US 2019/0170543 A1 Jun. 6, 2019

(51) Int. Cl.
*G01D 7/00* (2006.01)
*A47K 7/03* (2006.01)
*A47K 7/02* (2006.01)

(52) U.S. Cl.
CPC .............. *G01D 7/005* (2013.01); *A47K 7/02* (2013.01); *A47K 7/03* (2013.01)

(58) Field of Classification Search
CPC ............. G01D 7/005; A47K 7/03; A47K 7/02
See application file for complete search history.

(56) References Cited

U.S. PATENT DOCUMENTS

| | | | | |
|---|---|---|---|---|
| 4,078,340 A * | 3/1978 | Klecker | ................. | A22C 11/00 51/295 |
| 5,906,834 A * | 5/1999 | Tseng | .................... | A46B 11/00 15/104.93 |
| 6,501,002 B1 * | 12/2002 | Roe | .......................... | A47K 7/00 422/402 |
| 6,536,975 B1 * | 3/2003 | Tufts | ...................... | A45D 34/04 401/133 |
| 7,476,047 B2 * | 1/2009 | Brunner | .................. | A47L 13/17 401/133 |
| 7,629,043 B2 * | 12/2009 | Lindsay | .................. | A47L 13/16 428/316.6 |
| 8,708,983 B2 * | 4/2014 | McDonald | .......... | A61M 35/003 604/310 |
| 2004/0179889 A1 | 9/2004 | Tufts et al. | | |
| 2005/0125926 A1 * | 6/2005 | Rekum | .................. | A47L 13/16 15/208 |
| 2005/0136238 A1 * | 6/2005 | Lindsay | .................... | B32B 5/18 428/304.4 |

(Continued)

FOREIGN PATENT DOCUMENTS

WO    WO 2017/205400 A1    11/2017

*Primary Examiner* — Nimeshkumar D Patel
*Assistant Examiner* — Tania Courson
(74) *Attorney, Agent, or Firm* — Arent Fox LLP

(57) ABSTRACT

A method for signifying a selected cumulative scrubbing action between a device and a surface, the cumulative scrubbing action being signified by a signaling element, wherein the signaling element is configured to provide an observable signal when the selected cumulative scrubbing action has been provided to the surface. The method may comprise applying scrubbing action to the signaling element to release and/or expose at least a first portion of an indicator, and observing the device and/or surface for the signal. The present disclosure also relates to signaling elements and devices for use according to the methods of the present disclosure, and to methods of preparing the same.

24 Claims, 11 Drawing Sheets

(56) References Cited

U.S. PATENT DOCUMENTS

| | | | |
|---|---|---|---|
| 2006/0246802 A1* | 11/2006 | Hughes | B32B 3/266 |
| | | | 442/327 |
| 2007/0022555 A1 | 2/2007 | Penzes | |
| 2007/0134045 A1* | 6/2007 | Holt | B08B 1/00 |
| | | | 401/7 |
| 2007/0148447 A1 | 6/2007 | Amundson et al. | |
| 2009/0110890 A1 | 4/2009 | Garza et al. | |
| 2013/0092543 A1* | 4/2013 | Heikenfeld | B01D 35/06 |
| | | | 204/554 |

* cited by examiner

METHOD AND DEVICES FOR SIGNIFYING SCRUBBING ACTION

BACKGROUND

In many applications, including the disinfection of skin surfaces, the cleansing of household and/or hospital surfaces, and the cleanup of hazardous materials, scrubbing action plays an important role in providing an acceptable result. For example, certain cleansing agents must be sufficiently scrubbed in order to provide acceptable cleansing. As such, it is often not acceptable to merely ensure that certain agents (e.g., cleansing agents) have been applied to a surface. Rather, it is important to ensure that an adequate scrubbing action has also been applied.

There is thus a need in the art for a reliable and efficient method for confirming if an adequate scrubbing action has been achieved on a surface, while also determining where on the surface the adequate scrubbing action has been provided.

SUMMARY

The present disclosure relates generally to a method for signifying a selected cumulative scrubbing action between a device and a surface. According to some aspects, the cumulative scrubbing action may be signified by a signaling element, wherein the signaling element is configured to provide an observable signal when a selected cumulative scrubbing action has been provided to the surface. The selected cumulative scrubbing action may correspond to the cumulative scrubbing action required by the device for optimum performance. According to some aspects, the method may comprise the application of scrubbing action to the signaling element to release and/or expose at least a first portion of an indicator, and observing the device and/or surface for the signal. The present disclosure also generally relates to signaling elements and devices for use according to the methods of the present disclosure, and to methods of making the same.

DETAILED DESCRIPTION OF THE INVENTION

Figure 1:
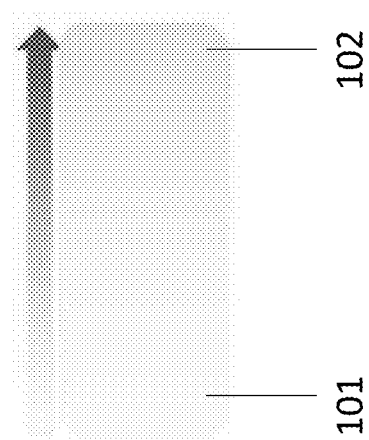
FIG. 1 shows an example of a signal provided by a visual indicator according to the present disclosure.

The present disclosure relates generally to a method for signifying a selected cumulative scrubbing action between a device and a surface. According to some aspects, the cumulative scrubbing action may be signified by a signaling element, wherein the signaling element is configured to provide an observable signal when a selected scrubbing action has been provided to the surface. The selected scrubbing action may correspond to the cumulative scrubbing action required by the device for optimum performance. According to some aspects, the method may comprise applying scrubbing action to the signaling element to release and/or expose at least a first portion of an indicator, and observing the device and/or surface for the signal. The present disclosure also generally relates to signaling elements and devices for use according to the methods of the present disclosure, and to methods of making the same.

The device according to the present disclosure may comprise any device configured to provide scrubbing action to a surface. Examples of devices useful according to the present disclosure include, but are not limited to, applicators, scrub brushes, swabs, swabsticks, scrubs, wipes, towelettes, cloths, dressing kits, gels/chips, sponges, gloves, and/or drapes (e.g., drapes configured to fit over or be held by one or more fingers, for example, worn over a finger with a ring-like attachment or worn over a single finger like a single finger of a glove or over several fingers like a mitten). As used herein, the term "applicator" refers to a device configured to apply a substance, the device having a handle, a container configured to contain a substance, and an application member.

According to some aspects, the device may comprise a ChloraPrep™ applicator and/or a similar antiseptic applicator. Example descriptions of such applicators may be found, for example, in copending U.S. application Ser. Nos. 14/529,753; 14/566,608; 14/595,084; and 15/163,500; and U.S. Pat. Nos. 5,690,958; 6,536,975; 8,708,983; 8,899,859; 9,119,946; 9,572,967; and 9,757,551, the disclosures of which are incorporated herein by reference in their entirety.

According to some aspects, the device may comprise a patient/topical wipe, a surgical/vascular access wipe, and/or a nasal, vaginal, oral, ocular, or rectal swab.

In some non-limiting examples, the device may comprise cloth, plastic, cellulose, paper, metal, gels, pastes, wood, glass, natural fibers such as cotton or linen, artificial fibers such as polyester, or a combination thereof. According to some aspects, the device may comprise woven and/or non-woven components.

According to some aspects, the device may be configured to cleanse a surface. As used herein, the term "cleanse" refers to the reduction, removal, and/or deactivation of contaminants on a surface.

Cleansing may comprise the application of scrubbing action to a surface to physically dislodge and/or remove contaminates from the surface. Alternatively or additionally, cleansing may comprise applying a cleansing agent to the surface. Examples of cleansing agents include, but are not limited to, an antimicrobial (e.g. antiseptic, antibiotic), disinfectant, deactivant, germicide, germicidal, biocidal, and/or biocide agent. Specific examples of cleansing agents according to the present disclosure include, but are not limited to, chlorhexidine and/or a salt thereof, octenidine and/or salt thereof, alcohol, iodine, and povidone iodine. According to some aspects, the cleansing agent may comprise chlorhexidine gluconate (CHG) and/or be alcohol-based, iodine-based, octenidine-based, chloroxylenol (PCMX)-based, triclosan-based, polyhexamethylene biguanide (PHMB)-based, ethylenediaminetetraacetic acid (EDTA)-based, and/or chloride-based and/or may comprise cyanoacrylate, cetrimide, bleach, ammonia/ammonium, vinegar, silver, Omiganan, Alexidine, and/or Olanexidine. It should be understood that any agent applied to a surface in order to reduce, remove, and/or deactivate contaminants on the surface may be used according to the present disclosure as long as the agent provides acceptable cleansing when provided with the selected scrubbing action.

According to some aspects, the device may be configured for use with a substance in addition to or instead of a cleansing agent. Examples of such substances include, but are not limited to, medicaments, such as anesthetics, analgesics, microbes (e.g., to replenish a patient's microbiome), healing agents, other growth factors (e.g., vascular growth factors), and any other drug to be administered locally (e.g., via a wipe or swab or other device). It should be understood that any substance that functions effectively in conjunction with the device may be used according to the present disclosure as long as the substance provides an acceptable function when provided with the selected scrubbing action.

The device may be configured to apply scrubbing action to a surface before, during, and/or after the cleansing agent and/or other substance (e.g., medicament) is applied to the surface. According to some aspects, the device may apply the cleansing agent and/or other substance to the surface. Additionally or alternatively, the device may be configured for use in conjunction with a separate device for applying and/or a separate composition comprising the cleansing agent and/or other substance. For example, the device may be used in conjunction with a separate composition which contains the cleansing agent and/or other substance, including toilet bowl cleansers, shower and/or other household cleaning agents, patient cleansing agents such as soaps, body washes, and shampoos, and combinations thereof.

According to some aspects, the device may be configured to collect a substance from a surface, such as in specimen collection. For example, the device may be configured for collecting specimens from nasal, oral, rectal, ocular, vaginal, topical, and/or mucosal areas.

According to some aspects, the surface may comprise a surface of a device (e.g., a medical device), a body of a patient (e.g., a patient's skin, such as prior to surgery, and/or mucosa, such as nasal mucosa, oral mucosa, and/or vaginal mucosa, for example, for nasal antisepsis, oral antisepsis, and/or vaginal antisepsis), or other surfaces such as a floor, a toilet bowl, shower and/or bathroom surfaces, kitchen surfaces, and/or hospital surfaces. It should be understood that any surface whereupon the device may operate may be used according to the present method.

According to some aspects, the method may comprise applying scrubbing action to a surface. As used herein, the term "scrubbing action" refers to the force of one moving surface (e.g., the surface of the device) against another surface. It should be understood that scrubbing action may be applied by scrubbing, wiping, rubbing, and/or blotting the device against a surface.

According to some aspects, the method may comprise applying a cumulative scrubbing action that is sufficient for providing optimum performance of the device and/or cleansing agent. It should be understood that the "optimum performance" of a device and/or cleansing agent is dependent on the specific device and/or cleansing agent. For example, if the device and/or cleansing agent is configured to cleanse a surface, optimum performance may correspond to a desired level of decontamination. According to some aspects, the desired level of decontamination may be below 5.0 $ng/cm^2$, optionally below 4.0 $ng/cm^2$, optionally below 3.0 $ng/cm^2$, optionally below 2.0 $ng/cm^2$, optionally below 1.0 $ng/cm^2$, optionally below 0.5 $ng/cm^2$, optionally below 0.1 $ng/cm^2$, and optionally below 0.01 $ng/cm^2$. Additionally or alternatively, "optimum performance" may correspond to a percentage of the device's and/or cleansing agent's capacity for cleansing. For example, "optimum performance" may correspond to the device and/or cleansing agent providing 60% of its decontamination capacity, optionally 65%, optionally 70%, optionally 75%, optionally 80%, optionally 85%, optionally 90%, optionally 95%, optionally 96%, optionally 97%, optionally 98%, optionally 99%, and optionally 100%.

Cumulative scrubbing action may be dependent on one or more factors, such as the rate at which the device provides shear force to the surface and/or signaling element, the rate at which the device provides friction force to the surface and/or signaling element, the magnitude of the force used to apply the scrubbing action (e.g., the pressure of the device against the surface), the length of time the force is applied, the fluid properties of the cleansing agent and/or signaling element, or a cumulative combination thereof.

In one non-limiting example, the device may comprise an applicator configured to apply a cleansing agent. For example, the device may comprise a ChloraPrep™ applicator or a similar applicator configured to dispense a solution containing 2% w/v chlorhexidine gluconate (CHG) in 70% v/v isopropyl alcohol (IPA), wherein optimum performance occurs when the applicator has been scrubbed against the surface to be cleansed with a certain cumulative scrubbing action. In another non-limiting example, the device may comprise a wipe containing a cleansing agent wherein optimum performance occurs when the wipe has been scrubbed against the surface to be cleansed with a certain cumulative scrubbing action.

The method of the present disclosure further comprises observing a signaling element for a signal signifying that a selected cumulative scrubbing action has been achieved. According to some aspects, the signaling element may provide the signal on a device and/or on a surface. As such, the device and/or surface may be observed for the presence or absence of the signal provided by the signaling element The signaling element may be provided with the device. For example, if the device comprises an applicator, the signaling element may be provided with and/or within one or more ampoules and/or similar containers of the applicator. The one or more ampoules and/or similar containers may be the same one or more ampoules and/or similar containers that contain the cleansing agent and/or other substance (e.g., medicament) and/or may be different. For example, the signaling element may be provided in a separate ampoule than the cleansing agent and/or other substance, wherein the applicator is provided with a first actuator to release the signaling element and a second actuator to release the cleansing agent and/or other substance. Alternatively or additionally, the applicator may compromise an actuator configured to release both the signaling element and the cleansing agent and/or other substance.

Additionally or alternatively, the signaling element may be provided with any portion of the applicator that allows the signaling element to signify scrubbing action. For example, according to some aspects, the applicator may comprise one or more fluid metering devices, such as a sponge, plug, or pledget, or other porous material. For example, the fluid metering device may be positioned between an application member of the applicator and one or more ampoules and/or similar containers for containing the cleansing agent and/or other substance. The fluid metering device may, for example, be configured to control the rate at which the cleansing agent and/or other substance flows from the one or more ampoules and/or similar containers to the application member, provide dye to the cleansing agent, and/or prevent shards of glass from ampoules broken during device activation from pushing through the application member during use of the applicator. According to some aspects, the fluid metering device may be provided with the signaling element (e.g., via impregnation) such that the signaling element contacts the cleansing agent and/or other substance as the cleansing agent and/or other substance flows through the fluid metering device. Alternatively or additionally, the signaling element may be provided with the application member of the applicator (e.g., via impregnation and/or as a layer of the application member).

It should be understood that the signaling element may be impregnated within, embedded within, contained within, and/or provided as a layer on the surface of any of the devices disclosed herein. It should also be understood that if a cleansing agent and/or other substance (e.g., a medicament) is provided with the device, the signaling element may be provided as part of a solution comprising the cleansing agent and/or other substance. Alternatively or additionally, the signaling element may be provided as part of a separate solution.

The signaling element may be provided as part of a secondary component. As used herein, the term "secondary component" refers to any component that is not provided with the device. For example, the secondary component may refer to a solution comprising the cleansing agent and/or other substance (e.g., medicament) that is applied to a surface prior to the device applying scrubbing action (e.g., a pretreatment solution). The secondary component may alternatively or additionally comprise a secondary device configured to administer the signaling element to the surface prior to the device applying scrubbing action. Examples or secondary components useful according to the present disclosure include, but are not limited to, liquids, gauzes, sponges, foams, gels, and combinations thereof.

The signaling element comprises one or more indicators. As used herein, the term "indicator" refers to the observable portion of the signaling element, that is, the portion of the signaling element that functions as the signal. The signal may be distinct from other components of the signaling element and/or device and/or the cleansing agent or other substance in one or more of color, taste, and smell. For example, the signal may provide a first visual indicator having a first color, wherein the first color is different than a second color, the second color being the color provided by a cleansing agent. In this way, a user may be able to distinguish where on a surface, for example, the cleansing agent has been applied but has not been sufficiently scrubbed, by individually visualizing the cleansing agent and the signal. According to some aspects, the first color may be colorless, i.e. clear. According to some aspects, the second color may modify or remove the appearance of the first color.

The indicator may comprise a visual indicator. Examples of visual indicators useful according to the present disclosure include, but are not limited to, a colorant or colorant precursor such as a dye, pigment, tint, and/or chromogen, a fluorescent indicator, a chemiluminescent indicator, and combinations thereof. For example, the colorant may comprise one or more Food, Drug, and Cosmetic (FD&C) approved color additives, such as FD&C Blue No. 1, FD&C Blue No. 2, FD&C Green No. 3, FD&C Red No. 3, FD&C Blue No. 1, FD&C Red No. 40, FD&C Yellow No. 5, FD&C Yellow No. 6, Oil Red Orange MX-465, and Oil Amber XA MX-166A.

For example, as shown in FIG. 1, the signaling element may be configured such that when a device does not provide the selected cumulative scrubbing action, the device stains a surface a first color 101 corresponding to, for example, the color of the cleansing agent. However, when the device provides the selected cumulative scrubbing action, the signaling element may be observed as a stain on the surface having a second color 102 corresponding to the color of the indicator or corresponding to the color of the combination of the indicator and the cleansing agent.

The indicator may comprise an aromatic indicator. The aromatic indicator may comprise fragrances, perfumes, or other aromatic substances Examples or aromatic indicators useful according to the present disclosure include, but are not limited to, essential oils such as D-limonene, camphor, eucalyptus, peppermint, menthol, lavender, and combinations thereof, and/or homologues, derivatives, chemical variations, and combinations thereof.

The indicator may comprise a flavor. Examples of flavors include, but are not limited to, any molecule configured to provide the sensation of taste, such as a peppermint, bubble gum, and/or lemon taste.

According to some aspects, the signaling element may be configured to release and/or expose at least one indicator when a selected cumulative scrubbing action has been achieved, thereby providing the signal.

The release and/or exposure may be a direct response to the selected cumulative scrubbing action. For example, the signaling element may comprise a degradable component wherein the degradable component is configured to constrain the indicator. As used herein, the term "constrain" refers to the inhibition of an action from taking place, for example, inhibiting the indicator from providing an observable signal. It should be understood that the degradable component may constrain the indicator, for example, by physically binding the indicator, by physically hiding the signal provided by the indicator, and/or any other means of inhibiting the indicator from providing the observable signal.

According to some aspects, the degradable component may be configured such that a selected cumulative scrubbing action changes the mechanical properties of the component, thereby releasing and/or exposing the indicator when the selected cumulative scrubbing action has been achieved. According to some aspects, the indicator provides an observable signal when it has been released and/or exposed by the degradable component.

According to some aspects, the signaling element may provide the signal in indirect response to the selected cumulative scrubbing action. For example, in one non-limiting example, the signaling element may comprise a degradable component, wherein the degradable component is sensitive to the effects of scrubbing action (e.g., sensitive to the mechanical stress or heat generated by a selected cumulative scrubbing action), thereby releasing and/or exposing the indicator when the selected cumulative scrubbing action has been achieved.

The signaling element may comprise a microcapsule, microbead, microsphere, microparticle, capsule, bead, particle, sphere, granule, vesicle and/or a combination thereof. The signaling element may comprise a core comprising an indicator encapsulated by a shell, wherein the shell comprises a degradable component. The degradable component may comprise at least one material that is sensitive to scrubbing action such that when the signaling element is subjected to a selected cumulative scrubbing action, the degradable component releases and/or exposes the indicator (e.g., by tearing, rupturing, erosion, dissolution, and/or degradation of the microcapsule shell and/or by interfacial delamination).

According to some aspects, the microcapsule may have an average diameter of between 1 μm and 10 mm, optionally between 1 μm and 5 mm, optionally between 1 μm and 1 mm, optionally between 1 μm and 500 μm, and optionally between 1 μm and 100 μm. The microcapsules may have an average diameter from anywhere between 1 nm and 10 cm. According to some aspects, the microcapsules may have an average diameter of about 190 μm or about 241 μm.

The signaling element may comprise one or more layers provided on the device. According to some aspects, the signaling element may comprise an inner layer having an indicator and an outer layer having a degradable component. The degradable component may comprise at least one material that is sensitive to scrubbing action such that when the signaling element is subjected to a selected cumulative scrubbing action, the degradable component releases and/or exposes the indicator (e.g., by erosion, dissolution, and/or degradation of the second layer).

The signaling element may comprise an indicator housed in an orifice, cavity, and/or other such housing of a device and a layer comprising the degradable component, wherein the degradable component exposes and/or releases the indicator when the signaling element is subjected to a selected cumulative scrubbing action.

Examples of materials useful as part of the degradable component include, but are not limited to, gelatin, cellulose, polyethylene glycol, alginate, polyoxymethylene, urea, inert polymers, pH-sensitive polymers such as carboxylate and amino derivatives, polyvinyl alcohol, ethyl cellulose, cellulose acetate phthalate, and styrene maleic anhydride.

According to some aspects, the signaling element may comprise a multi-component, such as one multi-component layer, which functions as both the indicator and the degradable component disclosed herein. For example, the multi-component may provide an observable signal until it is subjected to a selected cumulative scrubbing action, wherein the selected cumulative scrubbing action degrades and/or erodes the multi-component. In this way, a user may, for example, be able to distinguish between a device that has been used (i.e., wherein the observable signal is reduced or absent) and a device that has not been used (i.e., wherein the observable signal is present and has not been reduced).

Figure 2B:
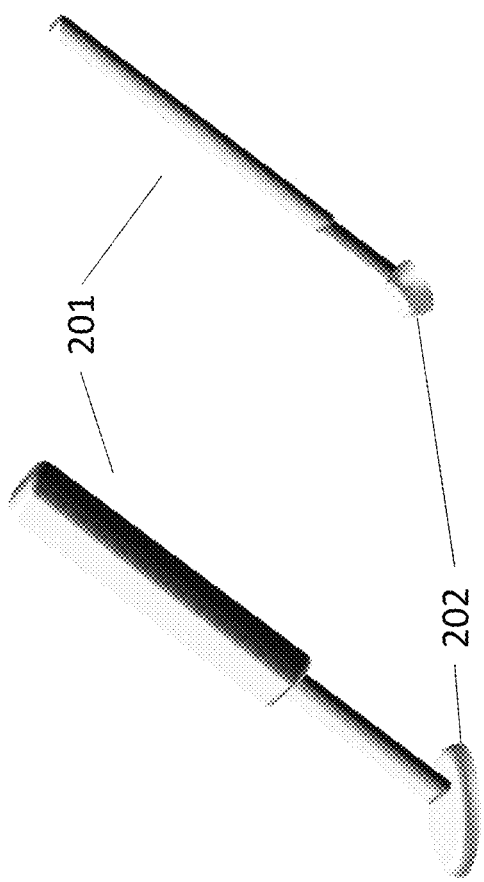
FIG. 2B shows an example of a device without a multi-component according to the present disclosure.
Figure 2A:
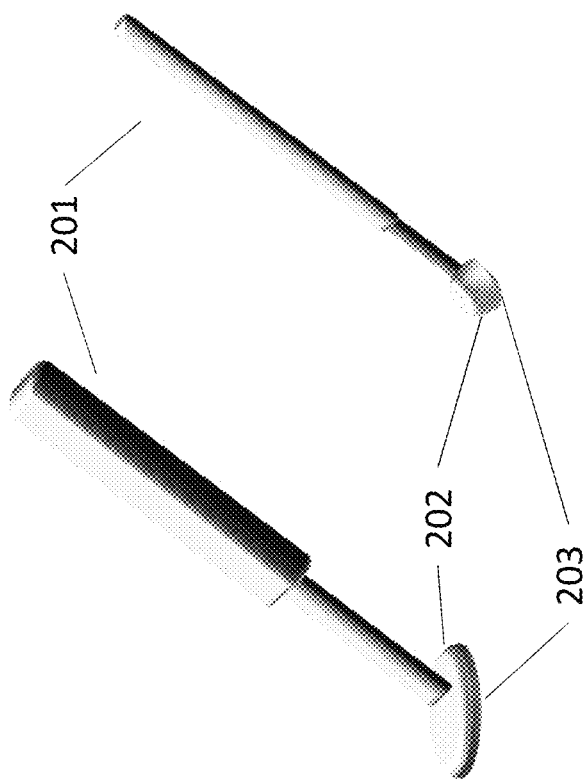
FIG. 2A shows an example of a device having a multi-component prior to a selected cumulative scrubbing action according to the present disclosure.

For example, as shown in FIG. 2A, a device 201, such as an applicator, may comprise an application member 202. The application member 202 may comprise a multi-component layer 203, wherein the multi-component provides a signal such as a gain or loss of color. The device 201 may be used to provide a cumulative scrubbing action to a surface such that when a selected cumulative scrubbing action has been achieved, the multi-component layer 203 is degraded and/or eroded away, for example, as shown in FIG. 2B. The color is thus not observable after the device has applied the selected cumulative scrubbing action.

Additionally or alternatively, a user may, for example, be able to determine when the selected cumulative scrubbing action has been achieved by observing the reduction and/or disappearance of the signal.

One or more characteristics of the degradable component and/or multi-component (e.g., polymer molecular weight, copolymer composition) may be selected in order to provide a selected sensitivity to scrubbing action. Alternatively or additionally, one or more other characteristics of the signaling element may be selected in order to provide the selected sensitivity to scrubbing action, for example, excipients used in conjunction with microcapsule (e.g., additives for stabilizing the microcapsules), manufacturing conditions of the signaling element, microcapsule size, and/or microcapsule shell thickness.

The signaling element may comprise a resin wherein one or more indicator molecules are reversibly bound to the resin to form a "signal-resinate complex." The resin may comprise an ion-exchange resin and/or any other material capable of reversibly binding indicator molecules or indicator-harboring entities, such as, for example, linker molecules bound to indicator molecules. The signaling element may be configured such that the indicator provides an observable signal when the one or more indicator molecules or indicator harboring entities are released from the resin and/or upon a shift in equilibrium between the bound and unbound state. The resin and/or indicator may be selected such that the resin releases the indicator molecules (and/or indicator-harboring entities) and/or an equilibrium shift occurs in direct and/or indirect response to the selected cumulative scrubbing action, for example, as described herein.

Figure 3:
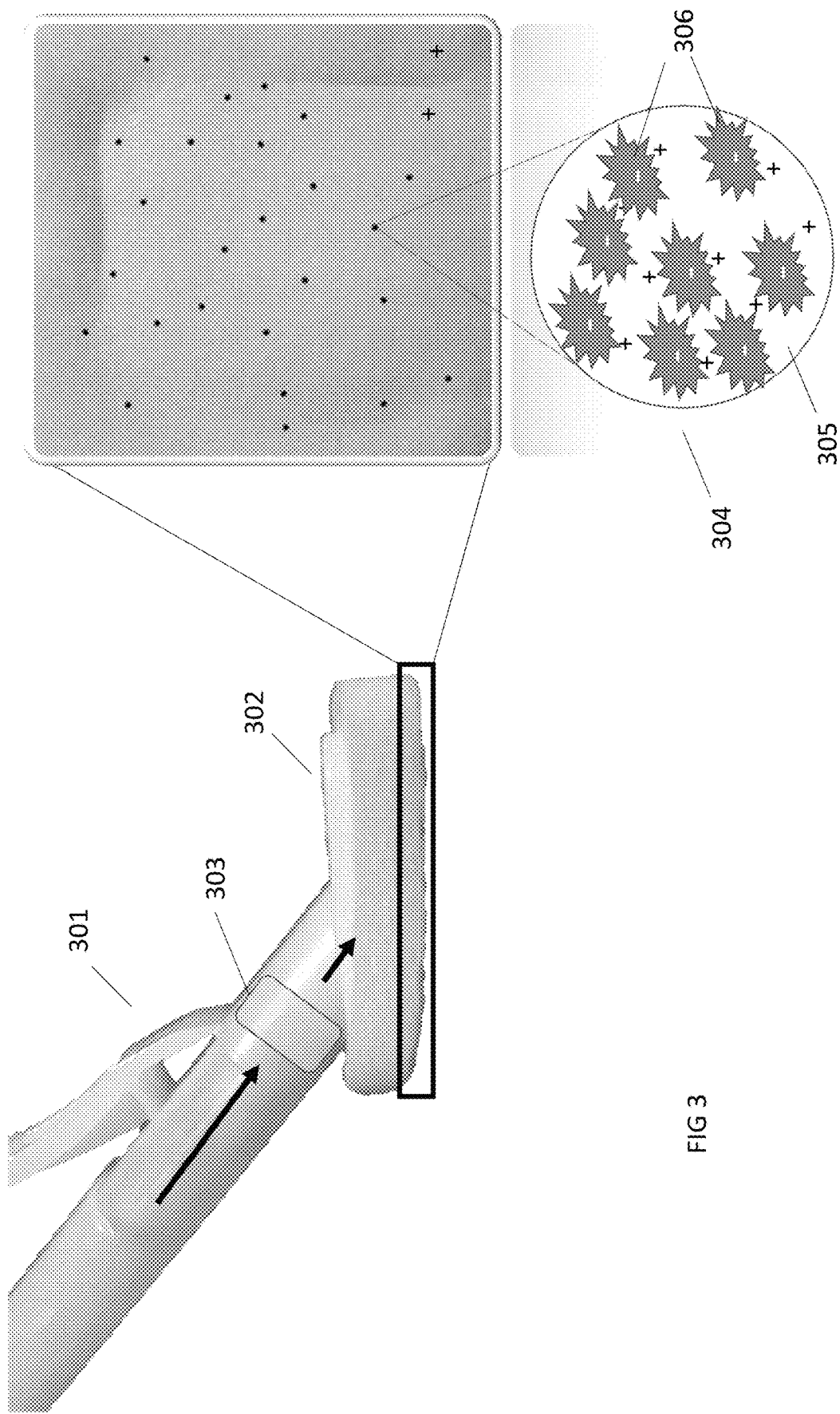
FIG. 3 shows an example of a device having a signaling element comprising an ion exchange resin according to the present disclosure.
Figure 4:
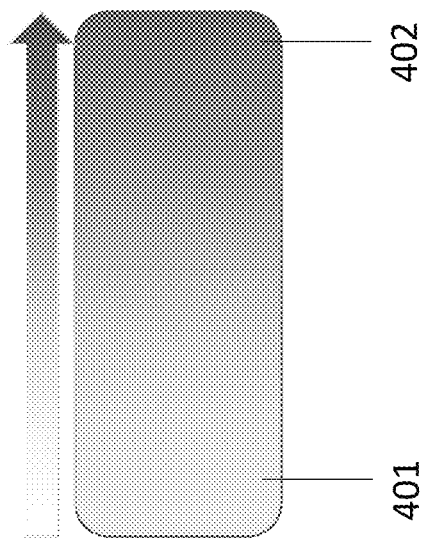
FIG. 4 shows an example of a signal provided by a device having a signaling element comprising an ion exchange resin according to the present disclosure.

For example, as shown in FIG. 3, the device 301, such as an applicator, may comprise an application member 302 and a device 303 configured to provide dye to a cleansing agent as it passes therethrough. The application member 302 may comprise a signaling element 304 having an ion exchange resin 305 and an indicator 306, such as a dye. As shown in FIG. 4, the signaling element may be configured such that when the applicator does not provide the selected cumulative scrubbing action, the applicator stains a surface a first color 401 corresponding to the color of the dye. However, when the applicator provides the selected cumulative scrubbing action, the applicator stains the surface a second color 402 corresponding to the color of the indicator.

Examples of suitable ion exchange resins include, but are not limited to a macroporous polymer matrix with quaternary amine functional group(s) (e.g., Duolite™ AP143-1083 or ScavengePore® phenethyl diethylamine), or a macroporous copolymer matrix with tertiary amine functional group(s) (e.g. Dowex® 66, AMBERLITE™ IRA96, or Amberlyst® A21).

According to some aspects, the signaling element may be configured to provide a signal in response to one or more secondary factors. As used herein, the term "secondary factor" refers to any factor other than scrubbing action. For example, the signaling element may be configured such that it provides a signal in the presence and/or absence of a particular composition (e.g., a cleansing agent and/or medicament), in the presence and/or absence of a selected contaminant.

In one non-limiting example, the signaling element may comprise an indicator that provides a signal when the indicator interacts with a selected cleansing agent and/or medicament. In this way, the signal is observable when the indicator has been released and/or exposed and has also interacted with the cleansing agent and/or medicament.

Additionally or alternatively, the signaling element may be configured such that the indicator is released and/or exposed when both the selected cumulative scrubbing action is achieved and the degradable component and/or signal-resinate complex interacts with a selected cleansing agent and/or medicament.

According to some aspects, the signal may comprise a color change visible on one or more portions of the device and/or on one or more portions of the surface. For example, when the indicator is released and/or exposed, a color change may be observed on the device and/or on the secondary component. Alternatively or additionally, when the indicator is released and/or exposed, the indicator may color all or a portion of the surface. For example, the indicator may stain and/or dye the surface where the selected cumulative scrubbing action has been achieved. In this way, the indicator may signal both that the selected cumulative scrubbing action has been achieved and where on the surface the selected cumulative scrubbing action has been provided. It should be understood that all or a portion of the signaling element (e.g., the indicator) may remain with the device and/or secondary component upon release and/or exposure of the indicator. Alternatively or additionally, all or a portion of the signaling element may be transferred to the surface prior to, during, or after the release and/or exposure of the indicator.

According to some aspects, the signal may comprise a change in scent or taste. For example, the signaling element may comprise an aromatic indicator and/or flavor indicator that functions as and/or functions with an aerosolized agent, such that the indicator is configured to pass through nasal passages to provide a taste or sensation of flavor upon release and/or exposure.

According to some aspects, the signaling element may be configured to provide a gradient signal. As used herein, the term "gradient signal" refers to a signal that changes in response to one or more factors. For example, the signaling element may be configured to provide a signal that is gradually observable.

According to some aspects, the gradient signal may become gradually more or less observable as cumulative scrubbing action increases. For example, the gradient signal may gradually change from one color (or colorless) to a different color (or colorless) as the cumulative scrubbing action increases to the selected cumulative scrubbing action. Alternatively or additionally, the gradient signal may become gradually more or less observable as the number of detectable factors (e.g., scrubbing action, the presence of a cleansing agent, etc.) increases. For example, the signal may gradually change from one color to another color as it is subjected to culminating factors. In this way, the signaling element may provide more than one signal. For example, the signaling element may provide a first signal at a first selected cumulative scrubbing action. The first signal may then gradually change to a second signal as the cumulative scrubbing action increases to a second selected cumulative scrubbing action. Alternatively or additionally, the signaling element may provide a first signal when a cleansing agent is detected. The first signal may then gradually change to a second signal as the signaling element is subjected to the selected cumulative scrubbing action.

According to some aspects, the signal may be permanent or temporary. For example, the signal may be temporary such that it weakens and/or disappears after it has been released and/or exposed.

The signaling element may be configured such that the signal weakens and/or disappears after a certain length of time. For example, the signal may weaken and/or disappear after 1 minute, optionally after 2 minutes, optionally after 3 minutes, optionally after 4 minutes, optionally after 5 minutes, optionally after 10 minutes, optionally after 15 minutes, optionally after 30 minutes, optionally after 60 minutes, optionally after 2 hours, optionally after 6 hours, optionally after 12 hours, optionally after 24 hours, optionally after 2 days, and optionally after 3 days. It should be understood that the length of time may be determined based on the specific application. It should be understood that the certain length of time may be selected such that, for example, the signal is detectable after the device is no longer in use and/or present. In this way, a non-user may be able to detect when a sufficient cumulative scrubbing action has occurred even if he or she did not apply the scrubbing action.

The signaling element may be configured such that the signal weakens and/or disappears as a function of contamination. For example, the signaling element may be configured such that the signal weakens and/or disappears upon a certain amount of bacterial regrowth.

The signaling element indicator may be configured such that the signal weakens and/or disappears as a function of one or more other factors. For example, the signaling element may be configured such that the signal weakens and/or disappears upon evaporation of a cleansing agent and/or medicament.

According to some aspects, the signaling element may be configured such that the signal is observable only on portions of the surface that have been subjected to the selected cumulative scrubbing action. For example, the signaling element may be configured to prevent the signal from leaching and/or moving to adjacent surface areas that have not been subjected to the selected cumulative scrubbing action. In some non-limiting examples, the signaling element may be configured to provide temporary or permanent adhesion to a surface (e.g., via film deposition), the signaling element may comprise microcapsules with a size sufficient to limit or prevent movement of the signaling element on the surface, and/or the signaling element may have a viscosity sufficient to limit or prevent movement of the signaling element on the surface (e.g., by the addition of a thickening agent, such as polyethylene glycol).

According to some aspects, the signaling element may comprise one or more components that are generally recognized as safe (GRAS) by the American Food and Drug Administration (FDA).

The present disclosure also generally relates to signaling elements and devices as described herein. The present disclosure also generally relates to methods of making the same.

According to some aspects, the method may comprise the preparation of microcapsules as described herein.

The method may comprise spray drying an indicator to prepare microparticles, and covering the microparticles with a layer of degradable component (e.g., gelatin or other polymer material) to create microcapsules.

The method may comprise suspending an oil-soluble indicator (e.g., a dye) within a water-soluble polymer unit (e.g., monomer). The indicator and polymer unit may then be blended together in a blender or reactor at a high speed (e.g., via a rotary blade) until beads or droplets of oil in water are formed at a selected size as a result of the high shear agitation. Droplet size may be selected by providing a certain speed and/or duration of agitation. A catalyst may then be added such that a water-soluble polymer begins to polymerize and precipitate out of solution. The water-soluble particle may fall upon and encapsulate the oil-soluble indicator as it precipitates out of solution. This effect may create a shell of polymer that surrounds the indicator-laden oil layer. Microcapsules may then be washed and dried. A similar process may also be applied for water-soluble indicator in non-soluble polymer, and/or through the formation of a water-oil-water emulsion with a middle organic phase that separates the indicator from the continuous phase (e.g., via emulsification/solvent evaporation wherein a water soluble dye could thereby be encapsulated in a polymer, such as poly(methyl methacrylate), or PMMA).

The method may comprise one or more of pan coating, air-suspension coating, centrifugal extrusion, vibrational nozzle, spray drying, ionotropic gelation, coacervation-phase-separation, interfacial polycondensation, interfacial cross-linking, in situ polymerization, matrix polymerization, spray congealing, micro-orifice system, rotary fluidization bed granulator method, spheronization, electrostatic, complex coacervation, interfacial polymerization, phase separation, submerged nozzle processes to extrude oil core material with polymer via a two fluid nozzle, fluid bed coating, spray chilling or spray cooling, extrusion coating, liposome entrapment, inclusion complexation, o/o/o (water miscible organic solvent, oil, external phase), solvent evaporation, and/or rotational suspension separation/the spinning disk method.

According to some aspects, the method may comprise making devices having one or more signaling element layers as described herein.

The method may comprise dipping or submerging a dyed or colored device having a first color (e.g., a wipe) into a degradable coating having a second color. Alternatively or additionally, the degradable coating may be sprayed onto the device.

The method may comprise one or more of two shot mold via injection molding, blow molding, thermoforming, pressure molding, electronic coating, fiber electrospinning and subsequent addition or direct addition via electrospinning process, cascading waterfall, co-extrusion, lamination, painting/coating, printing, fusing, silk screening, flexographic printing, extrusion, web offset printing, and/or 3D printing.

While the aspects described herein have been described in conjunction with the example aspects outlined above, various alternatives, modifications, variations, improvements, and/or substantial equivalents, whether known or that are or may be presently unforeseen, may become apparent to those having at least ordinary skill in the art. Accordingly, the example aspects, as set forth above, are intended to be illustrative, not limiting. Various changes may be made without departing from the spirit and scope of the disclosure. Therefore, the disclosure is intended to embrace all known or later-developed alternatives, modifications, variations, improvements, and/or substantial equivalents.

Thus, the claims are not intended to be limited to the aspects shown herein, but are to be accorded the full scope consistent with the language of the claims, wherein reference to an element in the singular is not intended to mean "one and only one" unless specifically so stated, but rather "one or more." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed as a means plus function unless the element is expressly recited using the phrase "means for."

Further, the word "example" is used herein to mean "serving as an example, instance, or illustration." Any aspect described herein as "example" is not necessarily to be construed as preferred or advantageous over other aspects. Unless specifically stated otherwise, the term "some" refers to one or more. Combinations such as "at least one of A, B, or C," "at least one of A, B, and C," and "A, B, C, or any combination thereof" include any combination of A, B, and/or C, and may include multiples of A, multiples of B, or multiples of C. Specifically, combinations such as "at least one of A, B, or C," "at least one of A, B, and C," and "A, B, C, or any combination thereof" may be A only, B only, C only, A and B, A and C, B and C, or A and B and C, where any such combinations may contain one or more member or members of A, B, or C. Nothing disclosed herein is intended to be dedicated to the public regardless of whether such disclosure is explicitly recited in the claims.

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, dimensions, etc.) but some experimental errors and deviations should be accounted for.

EXAMPLES

Example 1: Use of an Applicator in Conjunction with a Signaling Element

The applicator is actuated to release a chlorhexidine gluconate solution from an ampoule. Upon actuation, the chlorhexidine gluconate solution passes through a device impregnated with microcapsules according to the present disclosure. The applicator applies the chlorhexidine gluconate solution along with the microcapsules to the skin of a patent via an application member, and the application member is used to scrub the skin in a defined pattern (e.g., covering a certain area of the skin) as per device instructions. When sufficient scrubbing action has occurred, the microcapsules release dye, thereby temporarily staining the patient's skin. This signal thus demonstrates to the user and subsequent personnel that antiseptic action has been successfully performed and subsequent procedures can be commenced.

Example 2: Use of an Applicator in Conjunction with a Secondary Component Having a Signaling Element A paste comprising microcapsules according to the present disclosure is smeared on a surface to be cleansed. A cleansing tool is then utilized to apply cleanser and scrub the surface. When sufficient scrubbing action has occurred, the microcapsules release dye, thereby temporarily staining the surface. This signal thus demonstrates to the user and subsequent personnel that cleansing has been successfully performed.

Example 3: Use of an Applicator in Conjunction with a Secondary Component Having a Signaling Element and a Cleansing Agent A solution comprising microcapsules according to the present disclosure and a cleansing agent is applied to a surface to be cleansed. A cleansing tool is then utilized to scrub the surface. When sufficient scrubbing action has occurred, the microcapsules release dye, thereby temporarily staining the surface. This signal thus demonstrates to the user and subsequent personnel that cleansing has been successfully performed.

Example 4: Use of an Applicator in Conjunction with a Secondary Component Having a Signaling Element and with a Separate Cleansing Agent A solution comprising a cleansing agent is applied to (e.g., sprayed on) a surface. Then, a solution comprising microcapsules according to the present disclosure is applied to the surface to be cleansed. A cleansing tool is then utilized to scrub the surface. When sufficient scrubbing action has occurred, the microcapsules release dye, thereby temporarily staining the surface. This signal thus demonstrates to the user and subsequent personnel that cleansing has been successfully performed.

Example 5: Use of an Applicator in Conjunction with a Cleansing Agent

A solution comprising a cleansing agent is applied to (e.g., sprayed on) a surface. Then, an applicator is actuated to release microcapsules according to the present disclosure from an ampoule to the surface to be cleansed. The applicator is then utilized to scrub the surface. When a sufficient cumulative scrubbing action has occurred, the microcapsules release dye, thereby temporarily staining the surface. This signal thus demonstrates to the user and subsequent personnel that cleansing has been successfully performed.

Example 6: Deactivation of Hazardous Material Using Gradient Signal

A solution comprising a deactivation agent and microcapsules according to the present disclosure is applied to a surface that has been contaminated with hazardous material. A scrubbing tool is then utilized to scrub the surface. When sufficient scrubbing action has occurred in the presence of the deactivation agent, a first portion of the microcapsules release dye, thereby temporarily staining the surface with a first signal (i.e., a first color). The first signal thus demonstrates to the user that the contaminant has been successfully deactivated.

Then, a cleansing step is performed, wherein a cleansing agent is applied to the surface and the scrubbing tool is utilized to scrub the surface. When sufficient scrubbing action has occurred in the presence of the cleansing agent, a second portion of the microcapsules releases dye, and the first color temporarily stained on the surface gradually changes to a second color (i.e., a second signal). The second signal thus demonstrates to the user and subsequent personnel that cleansing has been successfully performed.

Example 7: Preparation and Use of a Degradable Layer

First, D&C Yellow No. 8-loaded ion exchange resin was prepared and adsorbed on to the foam applicator pad of a 1 mL ChloraPrep applicator. A layer of ethyl cellulose was added by dunking the resinate-loaded foam pads in an alcoholic solution of ethylcellulose and, and the foam pad was allowed to dry. An applicator prepared in the same manner, but lacking an ethylcellulose layer served as a control.

Figure 5:
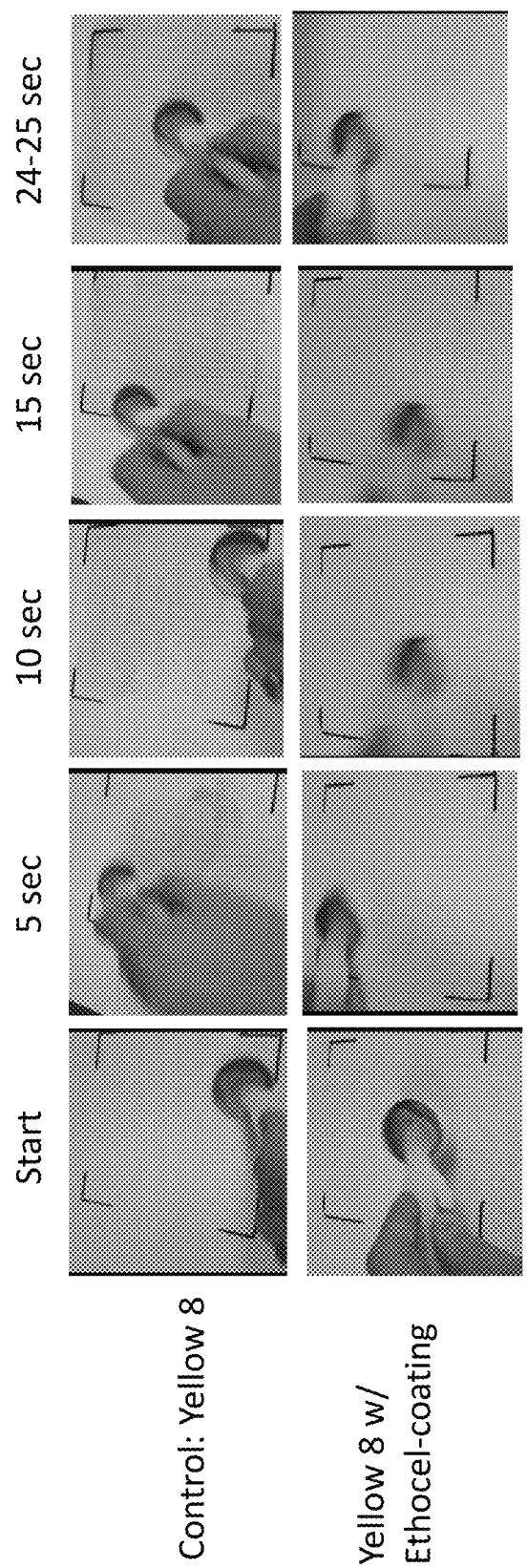
FIG. 5 shows a photograph of the effects of the applicator prepared and used according to Example 7.

As shown in FIG. 5, the ethyl cellulose coated device provided a first pale color when pressure was applied. This color was distinct from an intense second color provided by the control (no ethyl cellulose coating) when the same pressure was applied. Moreover, the color change provided by the microcapsules was more gradual than the color change provided by the control. It was thus concluded that the layer of ethyl cellulose—according to the present disclosure—is capable of providing a gradient signal (e.g., a gradual accumulation of the first color) as a function of applied scrubbing action.

Example 8: Preparation of Microcapsules

Figure 6A:
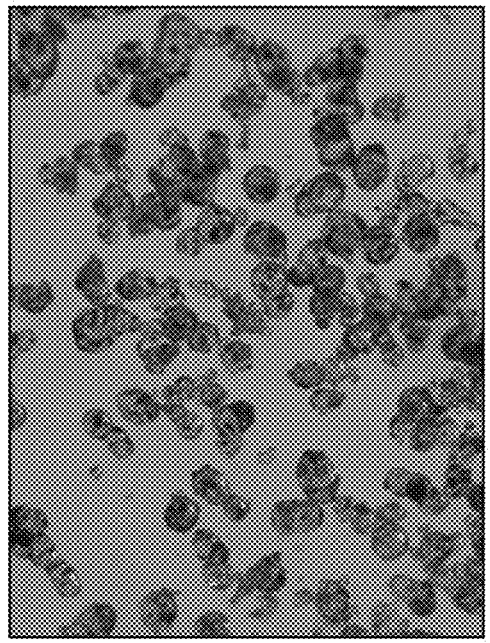
FIG. 6A shows the microcapsules prepared according to Example 8.
Figure 6B:
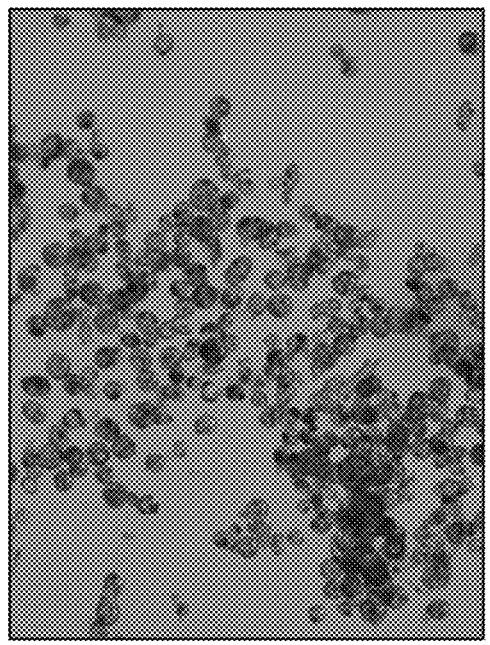
FIG. 6B shows the microcapsules prepared according to Example 8.

Microcapsules according to the present disclosure were prepared using FD&C Yellow No. 6 as an indicator and ethyl cellulose as a degradable element. As shown in FIGS. 6A and 6B, the microcapsules were prepared using either a 40:1 w/w ratio of ethyl cellulose to FD&C Yellow 6 (FIG. 6A) or a 20:1 w/w ratio (FIG. 6B). Both preparations provided FD&C Yellow #6 encapsulated in ethyl cellulose shells (microcapsules).

Example 9: Use of Microcapsules

First, 75 mg of the microcapsules prepared according to Example 7 (using a 20:1 ratio) was applied to each of a first surface and a second surface. FD&C Yellow 6 was applied to a third surface as a control. Then, a 1 mL ChloraPrep™ applicator was used to apply either hard pressure or soft pressure to the first or second surface, respectively, for 15 seconds following activation of the device. Soft pressure was applied to the control surface using a 1 mL ChloraPrep™ applicator following activation of the device.

Figure 7:
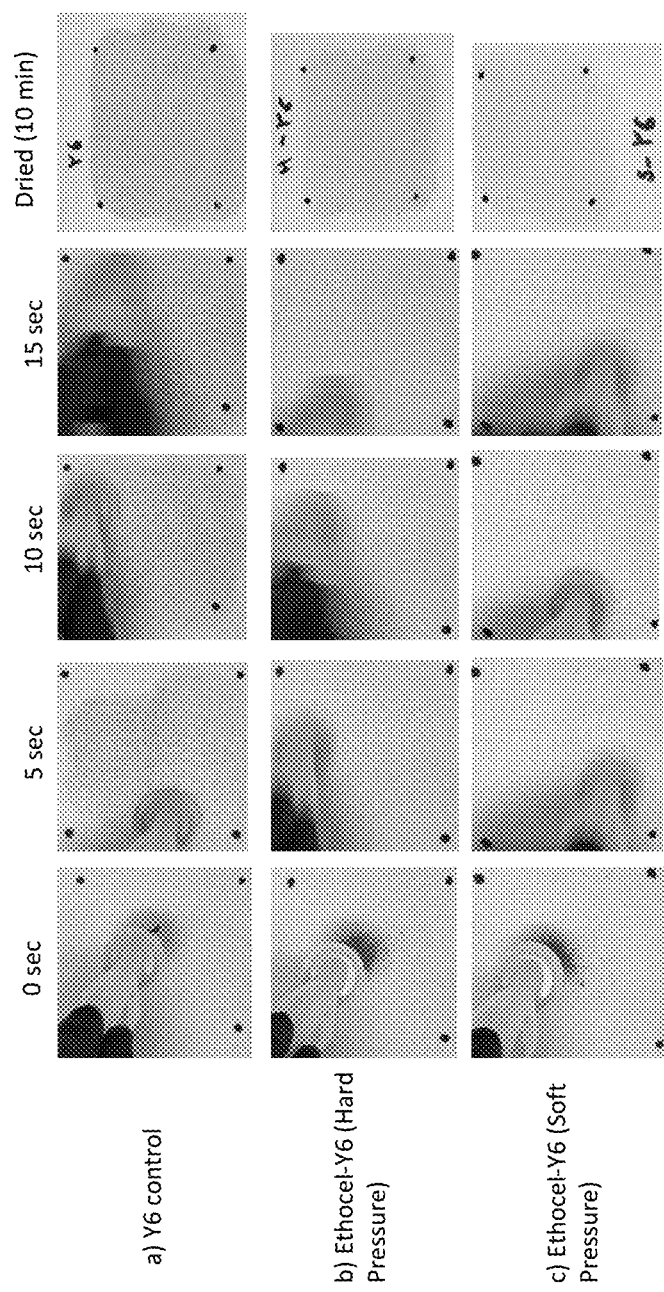
FIG. 7 shows a photograph of the effects of microcapsules used according to Example 9.

As shown in FIG. 7, the microcapsules provided a first color (dark yellow) when hard pressure was applied. This color was distinct from a second color (light yellow) provided when soft pressure was applied. The second color was also distinct from the color (faint yellow) provided by the control. It was thus concluded that the microcapsules according to the present disclosure are capable of providing a signal (e.g., the first color) when a selected cumulative scrubbing action has been achieved, wherein the selected cumulative scrubbing action is at least a function of pressure. In addition, it was determined that this signal was gradient, as the signal changed from one color (light yellow) to a different color (dark yellow) as it was subjected to an increase in pressure.

Example 10: Use of Microcapsules

First, 75 mg of the microcapsules prepared according to Example 7 (using a 20:1 ratio) was applied to a surface. Then, a 1 mL ChloraPrep™ applicator was used to apply hard pressure to the entire surface for 20 seconds. An additional 40 seconds of hard pressure was applied to only one half of the surface (resulting in 60 seconds total).

Figure 8:
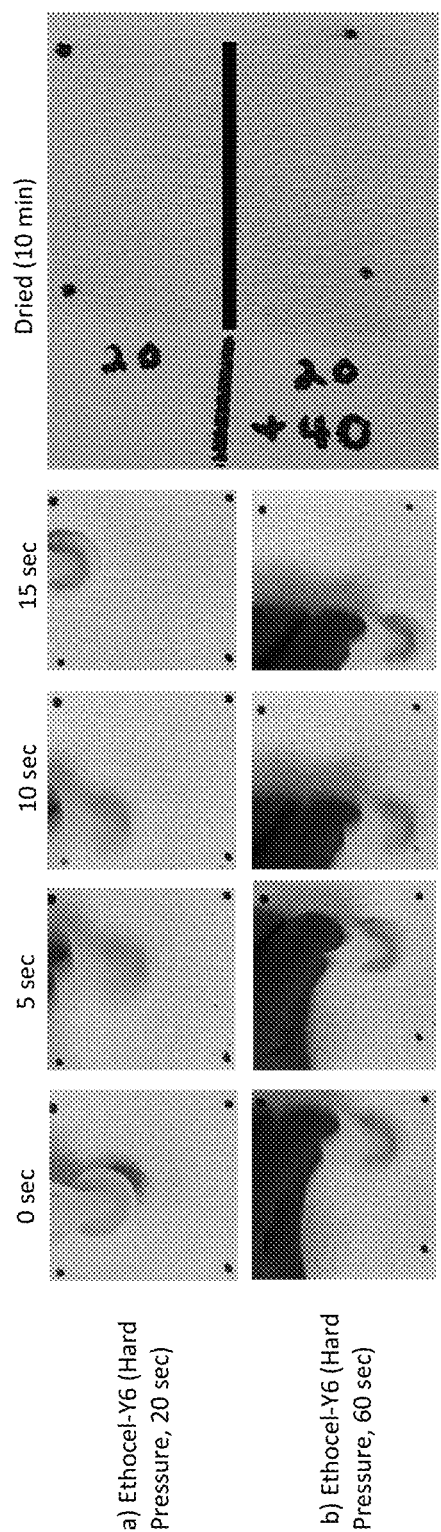
FIG. 8 shows a photograph of the effects of microcapsules used according to Example 10.

As shown in FIG. 8, the microcapsules provided a first color (light yellow) when hard pressure was applied for 20 seconds. This color was distinct from a second color (dark yellow) provided when hard pressure was applied for 60 seconds. It was thus concluded that the microcapsules according to the present disclosure are capable of providing a gradient signal (e.g., a gradual color changes to the first color, and then a gradual color change to the second color) when a selected cumulative scrubbing action has been achieved, wherein the cumulative scrubbing action is a function of time.

Example 11: Preparation of Microcapsules

Microcapsules according were prepared according to Example 7 using either a 40:1 ratio (resulting in a high shell thickness) or a 20:1 ratio (resulting in a low shell thickness). Then, 75 mg of each sample was applied to a first surface or a second surface. A 1 mL ChloraPrep™ applicator was then used to apply constant pressure to each surface for 40 seconds after application of the device.

Figure 9:
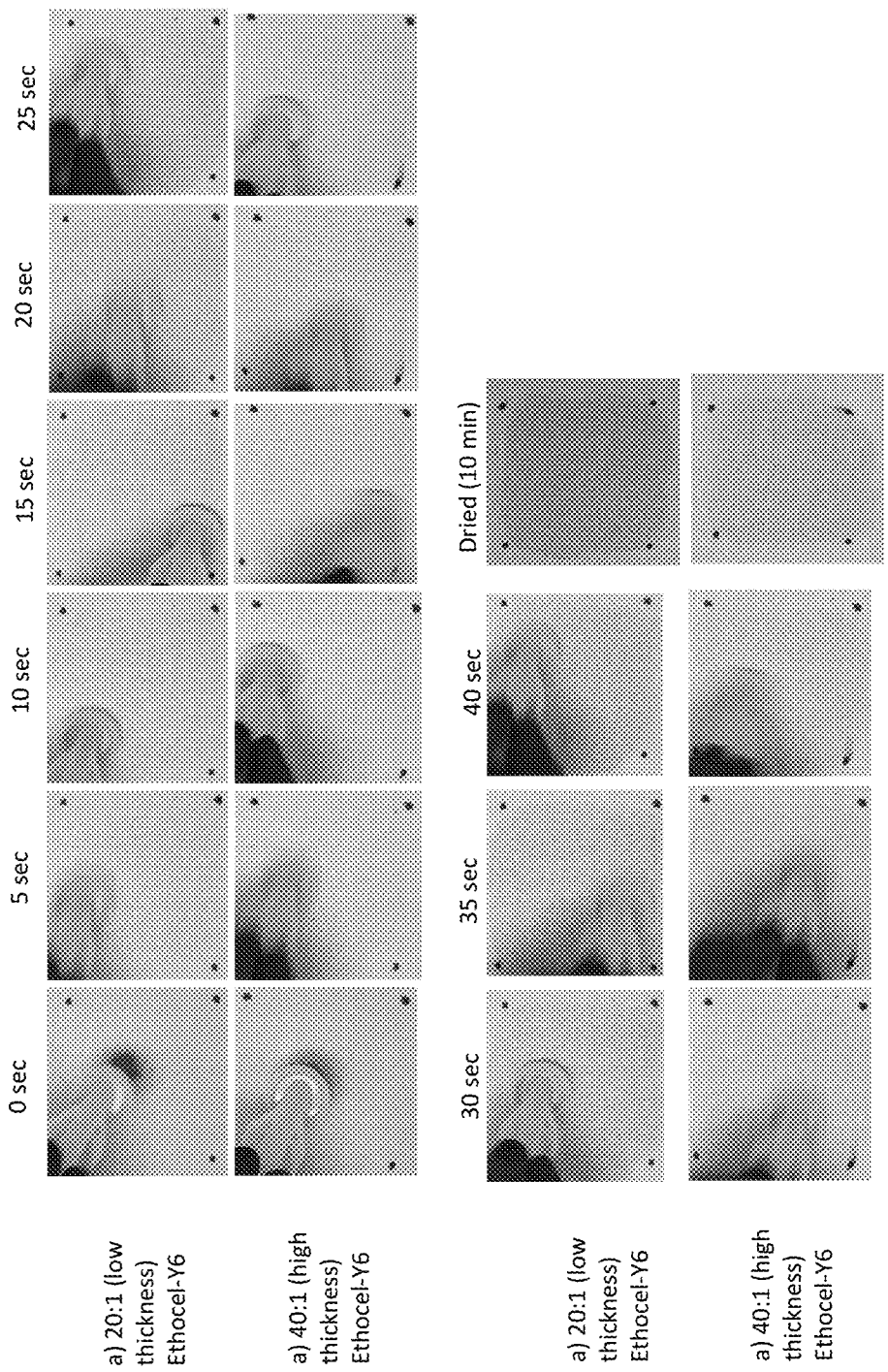
FIG. 9 shows a photograph of the effects of the microcapsules prepared and used according to Example 11.

As shown in FIG. 9, the high shell thickness microparticles provided a first color when pressure was applied. This color was distinct from a second color provided by the low shell thickness microcapsules when the same pressure was applied. It was thus concluded that shell thickness could be at least one factor that determines the sensitivity of the microcapsules to scrubbing action-triggered release of colorant. In particular, it was concluded that high shell thickness may provide microcapsules having a lower sensitivity to scrubbing action than microparticles having a low shell thickness. As such, low shell thickness microcapsules may provide a signal (e.g., the second color) at a lower selected cumulative scrubbing action than high shell thickness microcapsules.

Example 12: Preparation and Use of Device

An applicator was preparing having an application member and a device configured to provide D&C Yellow 8 to a chlorhexidine gluconate solution as the chlorhexidine gluconate solution passes therethrough. The application member comprised a signaling element having an ion exchange resin with FD&C Green No. 3 as an indicator reversibly bound thereto.

Two similar control applicators were also prepared. The first control did not comprise the signaling element. The second control did not comprise chlorhexidine gluconate.

Figure 10:
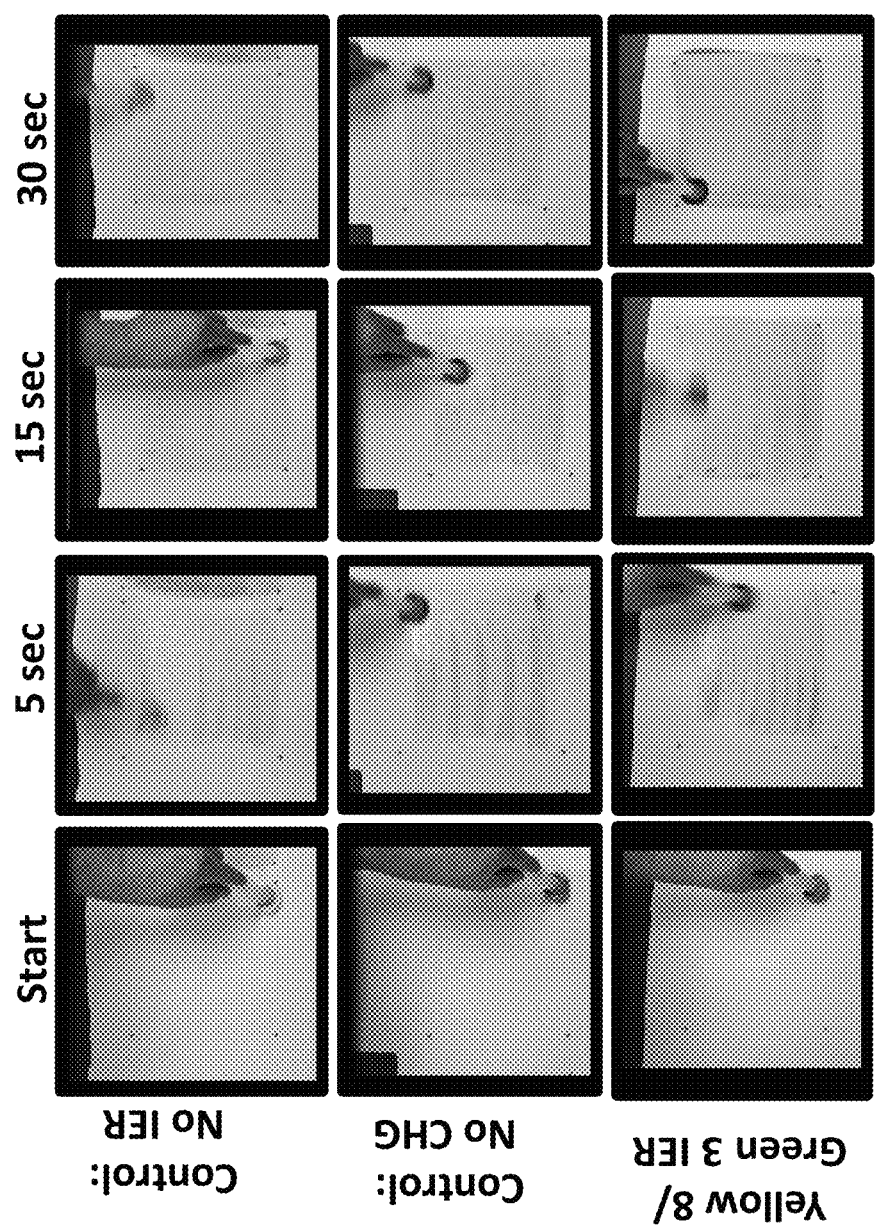
FIG. 10 shows a photograph of the effects of the device prepared and used according to Example 12.

Each of the applicators was scrubbed against a surface for 30 seconds following device activation. As shown in FIG. 10, the inventive applicator provided a first color (green) that is distinct from the color provided by the first control applicator (yellow) and the color provided by the second control applicator (yellow-green). It was thus concluded that a signaling element comprising an ion exchange resin could be sensitive to one or more factors other than scrubbing action (e.g., the presence of a cleansing agent such as chlorhexidine gluconate). In particular, this example shows that the signaling element provides a signal (i.e., the green color) when both pressure is applied and when chlorhexidine gluconate is present.

In addition, it was determined that this signal was gradient, as the single changed from one color (yellow-green) to a different color (green) as it was subjected to culminating factors (i.e., pressure and pressure with chlorhexidine gluconate, respectively).

Example 13: Preparation and Use Device

Four different applicators were prepared. First, an inventive applicator was prepared having an application member and a fluid metering device configured to provide D&C Yellow 8 to a chlorhexidine gluconate solution as the chlorhexidine gluconate solution passes therethrough. The application member comprised a signaling element having an ion exchange resin with FD&C Green No. 3 as an indicator reversibly bound thereto.

Three similar control applicators were also prepared. The first control applicator did not comprise the signaling element. The second control did not comprise the D&C Yellow 8 colorant. The third control did not comprise the D&C Yellow 8 or the chlorhexidine gluconate.

Figure 11:
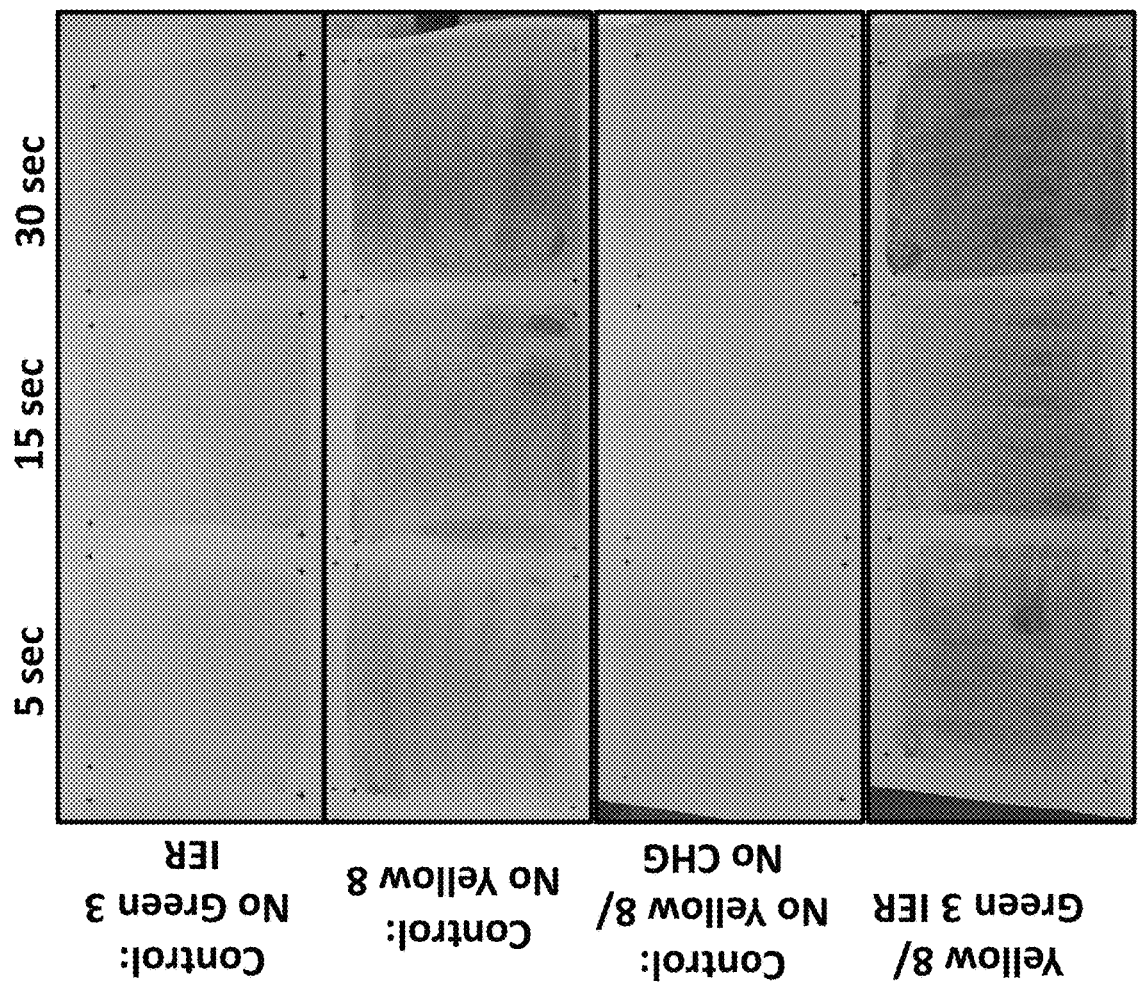
FIG. 11 shows a photograph of the effects of the device prepared and used according to Example 13.

Each of the applicators was scrubbed against a surface for 30 seconds. As shown in FIG. 11, the inventive applicator provided a first color (green) that was distinct from the color provided by the first control applicator (yellow) and the color provided by the second control applicator (blue). The third control applicator provided little color at all.

It was thus concluded that a signaling element comprising an ion exchange resin could be sensitive to one or more other factors (e.g., the presence of a cleansing agent such as chlorhexidine gluconate and/or the presence of a dye). In particular, this example shows that the signaling element provides a signal (i.e., the green color) when both pressure is applied and when chlorhexidine gluconate and dye is present.

In addition, it was determined that this signal was gradient, as the signal changed from one color (yellow-green) to a different color (green) as it was subjected to increasing scrubbing action (i.e., a longer scrub time).

The invention claimed is:

1. A method for signifying a selected cumulative scrubbing action comprising:
   applying a signaling element to a surface, the signaling element comprising an indicator configured to function as a signal when the selected cumulative scrubbing action is applied to the signaling element;
   applying scrubbing action to the signaling element to release and/or expose at least a first portion of the indicator; and
   observing the surface for a presence or absence of the signal provided by the indicator,
   wherein the signaling element comprises at least one of:
   (a) a degradable component constraining at least a portion of the indicator, wherein the degradable component is configured to degrade in response to the selected cumulative scrubbing action, and
   (b) a resin reversibly bound to at least a portion of the indicator and/or an indicator harboring entity harboring at least a portion of the indicator, wherein the resin is configured to release the indicator and/or indicator harboring entity in response to the selected cumulative scrubbing action.

2. The method according to claim 1, wherein the signaling element is configured such that the degradable component releases and/or exposes at least a first portion of the indicator when the selected cumulative scrubbing action is applied.

3. The method according to claim 2, wherein the signaling element comprises a core comprising the indicator, and wherein the degradable component is on an outer surface of the core.

4. The method according to claim 1, wherein the scrubbing action is applied using a device.

5. The method according to claim 4, wherein the signaling element is applied to the surface using the device.

6. The method according to claim 5, wherein the signaling element is provided with the device.

7. The method according to claim 4, wherein the device is configured to apply a cleansing agent to the surface.

8. The method according to claim 4, wherein the device is selected from the group consisting of an applicator and a wipe.

9. The method according to claim 1, wherein the signal is a gradient signal.

10. The method according to claim 1, wherein the signaling element is configured to release and/or expose at least a second portion of the indicator when the signaling element is subjected to a cleansing agent.

11. The method according to claim 1, wherein the signaling element comprises a colorant.

12. The method according to claim 1, wherein the surface is a patient's body.

13. A method for signifying a selected cumulative scrubbing action comprising:
applying scrubbing action to a surface using a device, wherein the device comprises a signaling element having an indicator configured to function as a signal when the selected cumulative scrubbing action is applied to the signaling element; and
observing the device for a presence or absence of the signal provided by the indicator,
wherein the signaling element comprises at least one of:
(a) a degradable component constraining at least a portion of the indicator, wherein the degradable component is configured to degrade in response to the selected cumulative scrubbing action, and
(b) a resin reversibly bound to at least a portion of the indicator and/or an indicator harboring entity harboring at least a portion of the indicator, wherein the resin is configured to release the indicator and/or indicator harboring entity in response to the selected cumulative scrubbing action.

14. The method according to claim 13, wherein the signaling element is provided as two layers on an outer surface of the device, wherein an inner layer comprises the indicator and an outer layer comprises the degradable component.

15. The method according to claim 13, wherein the signaling element is provided as one multi-component layer on an outer surface of the device, wherein the one multi-component layer comprises the indicator and the degradable component.

16. The method according to claim 13, wherein the device is selected from the group consisting of an applicator and a wipe.

17. The method according to claim 13, wherein the surface is a patient's body.

18. A device comprising a signaling element,
wherein the device is configured to apply scrubbing action,
wherein the signaling element comprises an indicator configured to function as a signal when a selected cumulative scrubbing action is applied to the signaling element;
wherein the signaling element is configured to release and/or exposes at least a first portion of the indicator to provide the signal in response to the selected cumulative scrubbing action, and
wherein the signaling element comprises at least one of:
(a) a degradable component constraining at least a portion of the indicator, wherein the degradable component is configured to degrade in response to the selected cumulative scrubbing action, and
(b) a resin reversibly bound to at least a portion of the indicator and/or an indicator harboring entity harboring at least a portion of the indicator, wherein the resin is configured to release the indicator and/or indicator harboring entity in response to the selected cumulative scrubbing action.

19. The device according to claim 18, wherein the signaling element comprises a core comprising the indicator, and the degradable component on an outer surface of the core.

20. The device according to claim 18, wherein the signaling element is provided as two layers on an outer surface of the device, wherein an inner layer comprises the indicator and an outer layer comprises the degradable component.

21. The device according to claim 18, wherein the device is configured to apply the signaling element to a surface.

22. The device according to claim 18, wherein the device further comprises a cleansing agent, and wherein the device is configured to apply the cleansing agent to a surface.

23. A signaling element comprising an indicator configured to function as a signal,
wherein the signaling element is configured to release and/or exposes at least a first portion of the indicator to provide the signal on a surface in response to a selected cumulative scrubbing action applied to the surface, and
wherein the signaling element comprises at least one of:
(a) a degradable component constraining at least a portion of the indicator, wherein the degradable component is configured to degrade in response to the selected cumulative scrubbing action, and
(b) a resin reversibly bound to at least a portion of the indicator and/or an indicator harboring entity harboring at least a portion of the indicator, wherein the resin is configured to release the indicator and/or indicator harboring entity in response to the selected cumulative scrubbing action.

24. The signaling element according to claim 23, wherein the signaling element comprises a core comprising the indicator, and the degradable component on an outer surface of the core.

* * * * *